US00PP22488P2

(12) United States Plant Patent
Shiozaki

(10) Patent No.: US PP22,488 P2
(45) Date of Patent: Feb. 7, 2012

(54) ***DICENTRA* PLANT NAMED 'FIRE ISLAND'**

(50) Latin Name: ***Dicentra peregrina*×*Dicentra exima***
Varietal Denomination: Fire Island

(76) Inventor: Akira Shiozaki, Fukagawa (JP)

( * ) Notice: Subject to any disclaimer, the term of this patent is extended or adjusted under 35 U.S.C. 154(b) by 0 days.

(21) Appl. No.: 12/807,291

(22) Filed: Sep. 1, 2010

(51) Int. Cl.
*A01H 5/00* (2006.01)

(52) U.S. Cl. ..... Plt./426
(58) Field of Classification Search ..... Plt./426
See application file for complete search history.

*Primary Examiner* — Susan McCormick Ewoldt
(74) *Attorney, Agent, or Firm* — Penny J. Aguirre

(57) ABSTRACT

A new cultivar of *Dicentra* plant, 'Fire Island', characterized by its numerous flowers that are pink in color, its very early flowering season, its multiple and short branches, its very resistance to diseases and high growing temperatures, and its vigorous growth habit during propagation, and its lack of seed production.

2 Drawing Sheets

Botanical classification: *Dicentra peregrina*×*Dicentra exima*.

Variety denomination: 'Fire Island'.

BACKGROUND OF THE INVENTION

The present invention relates to a new and distinct cultivar *Dicentra peregrina*×*Dicentra exima* plant, botanically known as *Dicentra* 'Fire Island' and will be referred to hereinafter by its cultivar name, 'Fire Island'. The new cultivar of *Dicentra* is a hardy herbaceous perennial grown for landscape use.

The new *Dicentra* was developed through on ongoing breeding program by the Inventor in Hokkaido, Japan to develop new cultivars of *Dicentra* with good vigor and long flowering periods. 'Fire Island' arose a cross make in June 2002 between an unnamed plant of *Dicentra peregrina* from the Inventor's breeding program as the female parent and an unnamed plant of *Dicentra exima* from the Inventor's breeding program as the male parent. 'Fire Island' was selected in June 2004 as a single unique plant from the above cross.

Asexual reproduction of the new cultivar was first accomplished by the Inventor by means of stem cuttings in December 2005 in Hokkaido, Japan. Asexual reproduction by cuttings and in vitro propagation has determined that the characteristics of the new cultivar are stable and are reproduced true to type in successive generations.

SUMMARY OF THE INVENTION

The following traits have been repeatedly observed over a period of eight years and represent the characteristics of the new cultivar. These attributes in combination distinguish 'Fire Island' as a new and unique cultivar of *Dicentra*.

1. 'Fire Island' exhibits flowers that are pink in color.
2. 'Fire Island' exhibits numerous flowers and flowers very early in the growth season.
3. 'Fire Island' is well branched with short branches.
4. 'Fire Island' is presumed sterile as no seed set has been observed.
5. 'Fire Island' has shown good disease resistance.
6. 'Fire Island' has shown good resistance to high temperatures.

7. 'Fire Island' has a vigorous growth habit during propagation.

'Fire Island' can be most closely compared to the cultivars 'Rekka' (U.S. Plant Pat. No. 20,058), 'Burning Hearts' (U.S. Plant Pat. No. 20,797) and 'Red Fountain' (U.S. Plant Pat. No. 21,269). 'Rekka' differs from 'Fire Island' in having darker pink flowers, less branching with longer branches, in having greater fragrance, in being less disease resistant, and by producing seeds. 'Burning Hearts' differs from 'Fire Island' in having flowers that are redder in color, in having less flowers, in having less branching with slightly longer branches, in flowering later, in being less disease resistant, and in having a slower growth habit during propagation. 'Red Fountain' differs from 'Fire Island' in having flowers that are redder in color, in having less branching with slightly longer branches, and in being less disease resistant.

BRIEF DESCRIPTION OF THE DRAWINGS

The accompanying colored photographs illustrate the overall appearance and distinct characteristics of the new *Dicentra*. The photographs were taken of a one year-old plant as grown outdoors in a three-liter container in De hoef, The Netherlands.

The photograph in FIG. 1 provides an overall view of 'Lemon Frost' in bloom.

Figure 1:
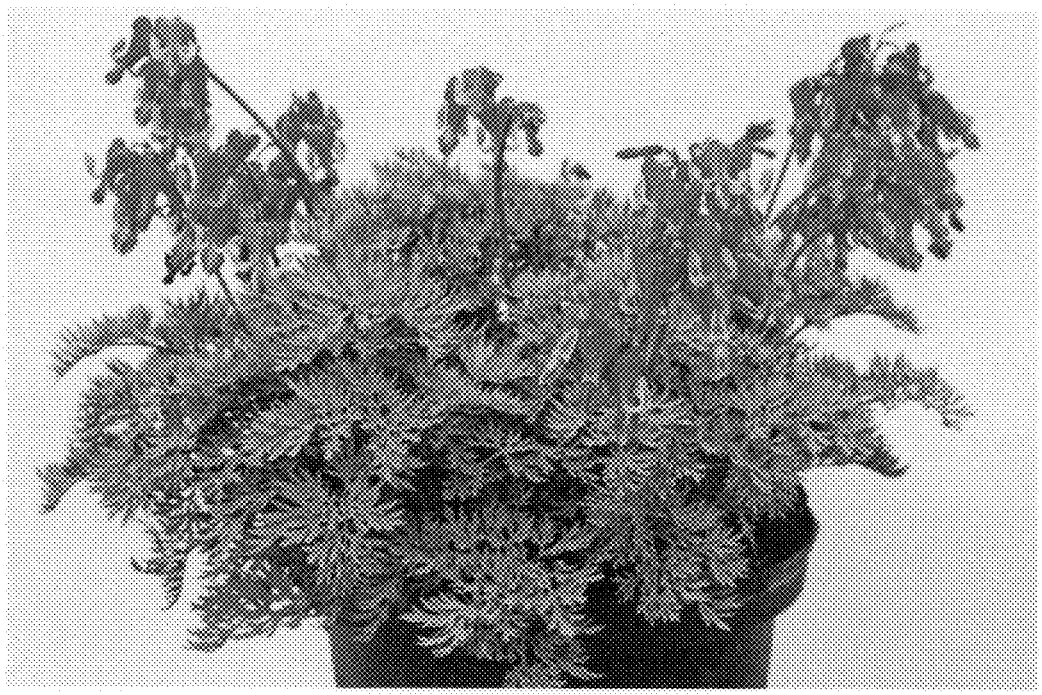
Figure 2:
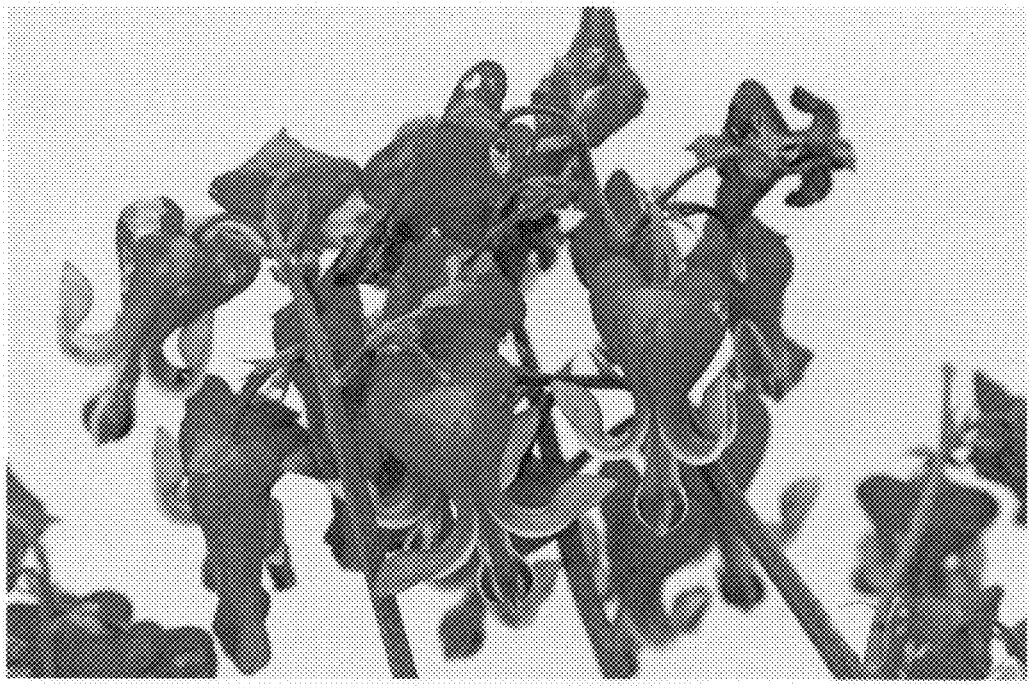

The photograph in FIG. 2 provides a close up view of the foliage of 'Fire Island'.

Figure 3:
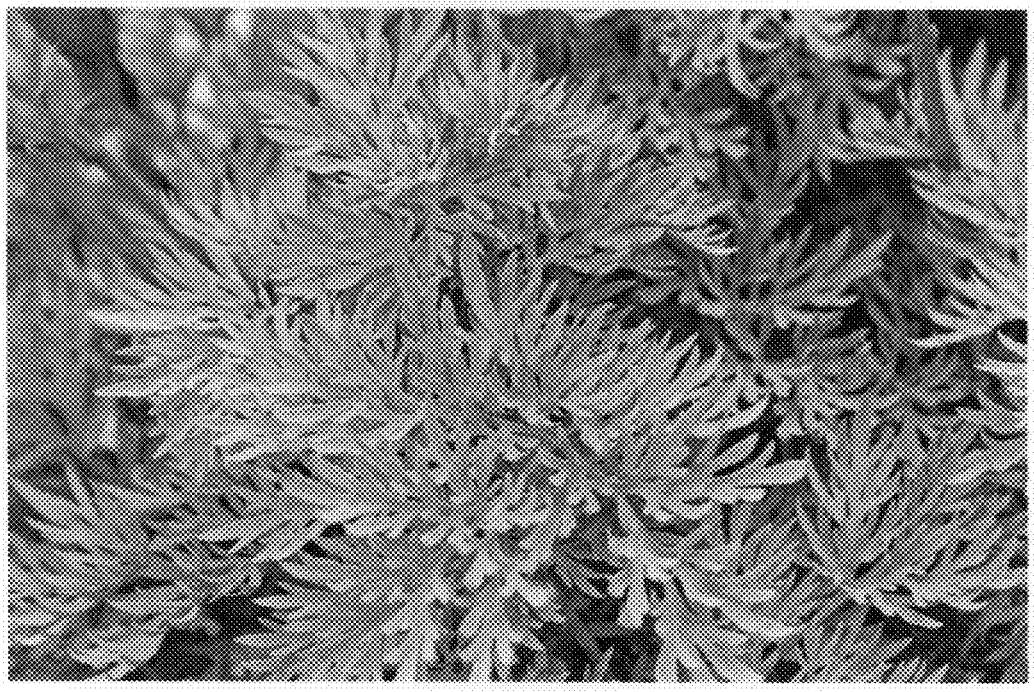

The photograph in FIG. 3 provides a close up view of the flowers of 'Fire Island'. The colors in the photograph may differ slightly from the color values cited in the detailed botanical description, which accurately describe the colors of the new *Dicentra*.

DETAILED BOTANICAL DESCRIPTION

The following is a detailed description of 1 year-old plants of the new cultivar as grown outdoors in July in De Hoef, The Netherlands. The plants were grown under average day temperatures ranging from 15° C. to 32° C. and average night temperatures ranging from 8° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from late spring (early May) to early summer (early July).

*Plant habit.*—Basal clump-forming, herbaceous perennial, mounded plant habit, flowering stems emerging above foliage.

*Height and spread.*—Reaches a height of 17.8 cm and a spread of about 31.4 cm.

*Cold hardiness.*—U.S.D.A. Zone 4.

*Heat tolerance.*—At least up to 35° C.

*Diseases and pests.*—No susceptibility or resistance to diseases or pests has been observed.

*Root description.*—Fleshy to fibrous, moderately dense, 199D.

*Propagation.*—Stem cuttings; root initiation occurs in 7 days and a rooted cutting will develop in a 72-cell plug in 14 days during the summer months, flowering plant in 9 cm containers or larger obtained in 20 weeks.

*Growth rate.*—Vigorous relative to *Dicentra.*

*Branching habit.*—Numerous basal branches.

Foliage description:

*Leaf division.*—Compound, 48 leaflets per leaf.

*Leaf arrangement.*—Basal clump.

*Leaf shape.*—Broad ovate.

*Leaf size.*—Average 8.4 cm in length, 8.2 cm in width.

*Leaflet size.*—Average 1.4 cm in length, 1.1 cm in width.

*Leaf number.*—Average of 24 per plant.

*Leaflet base.*—Short attenuate.

*Leaflet apex.*—Acute.

*Leaflet margin.*—Deeply incised to laciniate.

*Leaflet venation.*—Pinnate, upper surface 122A, lower surface between 122B and 188A.

*Leaflet surface.*—Smooth, dull, glabrous.

*Leaflet color.*—Upper surface; newly emerged between 136C and 189B, mature 122B, lower surface; newly emerged 189D, mature between 122B and 188B.

*Petiole.*—Average of 9.7 cm in length and 2 mm in width, 183B in color, surface glabrous.

*Durability of foliage to stress.*—Moderate.

Flower description:

*Inflorescence type.*—Compound panicle.

*Lastingness of inflorescence.*—10 days, self-cleaning.

*Time to flowering response.*—10 months.

*Inflorescence size.*—Average 6.1 cm in height excluding peduncle, 4.6 cm in width.

*Flower type.*—Zygomorphic and galeate.

*Flower aspect.*—Drooping.

*Flower number.*—About 8 flowers per inflorescence, up to 100 flowers and buds per plant with 40% of flowers open at any stage.

*Flower fragrance.*—Very faint, sweet.

*Flower buds.*—Narrow cordate, wider near the apex, average 2.1 cm in length, 1 cm in width, 58A and 58B in color, apex 69D with spots N79B.

*Flower size.*—About 2.3 cm in length, about 1.7 cm in diameter at widest part and 9 mm in diameter at narrowest part.

*Peduncles.*—Average 11.7 cm in length, 3 mm in diameter, emerging above foliage at an average angle of 15° from perpendicular.

*Peduncle strength.*—Moderate.

*Peduncle color.*—Base between 177A and 200B, apex N187A.

*Peduncle surface.*—Puberulent.

*Pedicels.*—Average of 8 mm in length, 1 mm in diameter, 50° from peduncle, N186C in color, puberulent surface.

*Tepals.*—4 arranged in 2 opposite pairs, pair of narrowest tepals fused at tip, tips of widest pair with recurved tips.

*Tepal shape.*—Narrowest tepals oblanceolate, widest tepals lanceolate.

*Tepal margin.*—Entire.

*Tepal apex.*—Rounded.

*Tepal surface.*—Smooth, dull, glabrous.

*Tepal size.*—Narrowest tepals; 2 cm in length and 4 mm in width, widest tepals; 2.3 cm in length and 8 mm in width.

*Tepal color.*—Upper surface when opening; base between 58A and 58B, apex 69D with spots N79B, upper surface fully opened; base 75C, apex N77B, lower surface when opening; base 58A, apex of narrowest pair N77B, apex of widest pair a color between 75A and 75B, lower surface fully opened; base 75C, apex N77B, upper and lower surface fading to color between 64A and 64B.

Reproductive organs:

*Gynoecium.*—1 Pistil, style is an average 1.0 cm in length, 152C in color, stigma is umbraculate and 11A in color, ovary is 147A in color.

*Androecium.*—6 stamens fused in 2 groups of 3, filaments are 1.7 cm in length, 75C and 75D in color, anthers are narrowly oblong, basifixed, 1 mm in length, 15A in color, pollen is low in abundance and 15A in color.

*Fruit.*—Fruit and seed production have not been observed, presumed sterile.

It is claimed:

1. A new and distinct variety of *Dicentra* plant designated 'Fire Island' as described and illustrated herein.

* * * * *